US010232193B2

(12) United States Patent
Iseki (10) Patent No.: US 10,232,193 B2
(45) Date of Patent: Mar. 19, 2019

(54) PARTICLE BEAM TREATMENT SYSTEM, PARTICLE BEAM TREATMENT MANAGEMENT SYSTEM AND METHOD

(71) Applicant: KABUSHIKI KAISHA TOSHIBA, Minato-ku (JP)

(72) Inventor: Yasushi Iseki, Kanagawa (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/795,788

(22) Filed: Oct. 27, 2017

(65) Prior Publication Data
US 2018/0064955 A1 Mar. 8, 2018

Related U.S. Application Data

(63) Continuation-in-part of application No. PCT/JP2016/002212, filed on Apr. 27, 2016.

(30) Foreign Application Priority Data

Apr. 28, 2015 (JP) ................................. 2015-092225

(51) Int. Cl.
*A61N 5/10* (2006.01)
*G06T 15/00* (2011.01)
(Continued)

(52) U.S. Cl.
CPC ............ *A61N 5/103* (2013.01); *A61N 5/1048* (2013.01); *G06T 7/74* (2017.01); *G06T 15/005* (2013.01);
(Continued)

(58) Field of Classification Search
CPC ............ A61N 5/103; A61N 2005/1061; A61N 2005/1074; A61N 2005/1088; G06T 7/74;
(Continued)

(56) References Cited

U.S. PATENT DOCUMENTS 9,192,781 B2 11/2015 Ichihashi et al.
9,199,093 B2 * 12/2015 Brusasco ............. A61N 5/1048
(Continued)

FOREIGN PATENT DOCUMENTS

JP H10-146395 A 6/1998
JP H10-309324 A 11/1998
(Continued)

OTHER PUBLICATIONS

Mori et al., "Patient Handling System For Carbon Ion Beam Scanning Therapy," Journal Of Applied Clinical Medical Physics, vol. 13, No. 6, 2012.

*Primary Examiner* — Nicole Ippolito
(74) *Attorney, Agent, or Firm* — Oblon, McClelland, Maier & Neustadt, L.L.P.

(57) ABSTRACT

According to an embodiment, a particle beam treatment system has: a CT device that is a three-dimensional image acquisition part installed in a treatment room for acquisition of a three-dimensional internal image on a day of treatment; a dose distribution display part that displays a dose distribution in the three-dimensional image acquired on the day of treatment and a dose distribution in treatment plan data designed in advance; a treatment management device that is a selection part to select whether or not to change the treatment plan data based on the dose distribution in the three-dimensional image acquired on the day of treatment and the dose distribution in treatment plan data designed in advance; and an irradiation part that irradiates an affected part with a particle beam according to the treatment plan data based on selection made by the treatment management device.

10 Claims, 7 Drawing Sheets

(51) Int. Cl.
  *G06T 7/73* (2017.01)
  *H04N 13/275* (2018.01)
(52) U.S. Cl.
  CPC ... *H04N 13/275* (2018.05); *A61N 2005/1061* (2013.01); *A61N 2005/1074* (2013.01); *A61N 2005/1088* (2013.01); *A61N 2005/1092* (2013.01); *G06T 2207/10121* (2013.01); *G06T 2211/40* (2013.01)
(58) Field of Classification Search
  CPC ......... G06T 15/005; G06T 2207/10121; G06T 2211/40; H04N 13/275
  USPC ................ 250/492.1, 492.3, 396 R, 397
  See application file for complete search history.

(56) References Cited

U.S. PATENT DOCUMENTS

| | | | |
|---|---|---|---|
| 2005/0197564 A1* | 9/2005 | Dempsey | A61B 5/055 600/411 |
| 2005/0201516 A1* | 9/2005 | Ruchala | A61N 5/103 378/65 |
| 2011/0049372 A1 | 3/2011 | Iseki et al. | |
| 2014/0019440 A1 | 1/2014 | Kim et al. | |
| 2016/0310761 A1* | 10/2016 | Li | A61N 5/1038 |
| 2017/0232274 A1* | 8/2017 | Isola | A61N 5/1031 600/1 |
| 2017/0330045 A1* | 11/2017 | Crosetto | A61B 6/5217 |

FOREIGN PATENT DOCUMENTS

| | | |
|---|---|---|
| JP | H11-299906 A | 11/1999 |
| JP | 4429839 B2 | 12/2009 |
| JP | 2011-050585 A | 3/2011 |
| JP | 2011-200542 A | 10/2011 |
| JP | WO 2011/162021 A1 | 12/2011 |
| JP | 2012-35072 A | 2/2012 |
| JP | 2014-136054 A | 7/2014 |
| JP | 2016-032506 A | 3/2016 |
| JP | 2016-129639 A | 7/2016 |
| WO | 2013/171631 A1 | 11/2013 |

* cited by examiner

PARTICLE BEAM TREATMENT SYSTEM, PARTICLE BEAM TREATMENT MANAGEMENT SYSTEM AND METHOD

CROSS-REFERENCE TO RELATED APPLICATIONS

This application is a continuation-in-part of prior International Application No. PCT/JP2016/002212, filed on Apr. 27, 2016 which is based upon and claims the benefit of priority from Japanese Patent Application No. 2015-092225, filed on Apr. 28, 2015, the entire contents of all of which are incorporated herein by reference.

FIELD

The embodiments of the present invention relate to a particle beam treatment system that irradiates, e.g., an affected part with a particle beam (hereinafter, also referred to simply as "beam") such as a heavy particle beam (e.g., carbon beam) or proton beam for the purpose of cancer treatment, and a particle beam treatment management system and method thereof.

BACKGROUND

For example, a particle beam irradiation method is currently used in cancer treatment. The particle beam irradiation method includes a method called broad beam method. In the broad beam method, a beam diameter is expanded to a size equal to or larger than the size of an affected part by a method called a wobbler method or a double scattering method. Further, in the broad beam method, a collimator limits an irradiation area to direct the beam in accordance with the shape of the affected part. However, the broad beam method cannot achieve three-dimensional exact matching of the beam to the affected part shape, and there is a limit on reduction in adverse effect on normal cells around the affected part.

In light of this, there has been developed a three-dimensional (3D) scanning irradiation method. In the 3D scanning irradiation method, irradiation is performed in such a manner as to three-dimensionally fill an affected part without a collimator. The particle beam treatment by this three-dimensional scanning irradiation method is performed in the following first to three steps.

In the first step, computed tomography (hereinafter, abbreviated as "CT") is performed for the purpose of making a treatment plan. A CT image obtained by the CT is used not only for making the treatment plan, but also for creating a reference image for positioning of the patient during treatment. The first step is generally performed on a previous day of the treatment day.

In the second step, the position of the patient is set. Specifically, the patient is placed on a treatment bed, and a mark formed on the surface of a fixing tool for fixing the patient is adjusted to the irradiation center. In this state, X-ray fluoroscopy is performed. Then, a fluoroscopic image obtained by the X-ray fluoroscopy and the reference image obtained from the CT image in advance are compared to calculate a positional deviation amount. Subsequently, the deviation amount is set to the treatment bed so as to make the fluoroscopic image and reference image agree with each other.

In the third step, irradiation of a particle beam is performed. Specifically, individual devices of an irradiation system are put into an irradiation enabled state after the setting of the patient's position, and then irradiation is started. The three-dimensional scanning irradiation method is a method that irradiates an affected part according to the treatment plan designed in advance based on the CT image.

However, according to the above procedure, the first step is conducted before the treatment day, so that the position of an affected part and the position of normal tissue may change depending on the conditions of body gas, digests, and excrement in the patient's body. In this case, even when the patient's position is reset to the treatment bed, there remains a problem concerning reliability of reproducibility of the position.

Further, in the second step, the treatment bed needs to be moved after the X-ray photography, so that a high requirement is placed on the positional accuracy of the treatment bed, with the result that daily (usually, in the morning before the start of the treatment) QA (Quality Assurance) test takes time. Further, after the treatment bed is moved, X-ray photography needs to be performed again in order to confirm that the set position is correct. As a result, it takes time to perform device setting for X-ray photography, and exposure dose of the patient is increased.

DETAILED DESCRIPTION

An object of the present embodiments is to provide a particle beam treatment system, a particle beam treatment management system, and a method of using the systems, which enable accurately irradiating an affected part with a particle beam even when the fixed position of the affected part or conditions of internal organs differ from the treatment plan designed in advance.

In order to solve the problems, there is presented an embodiment a particle beam treatment system comprising: a three-dimensional image acquisition part installed in a treatment room for acquisition of a three-dimensional internal image on a day of treatment; a dose distribution display part that is configured to display a dose distribution in the three-dimensional image acquired on the day of treatment and a dose distribution in treatment plan data designed in advance; a selection part that is configured to select whether or not to change the treatment plan data based on the dose distribution in the three-dimensional image acquired on the day of treatment and the dose distribution in treatment plan data designed in advance; and an irradiation part that is configured to irradiate an affected part with a particle beam according to the treatment plan data based on selection made by the selection part.

There is also presented an embodiment a particle beam treatment management system comprising: a three-dimensional image acquisition part installed in a treatment room for acquisition of a three-dimensional internal image on the day of treatment; a dose distribution display part that is configured to display a dose distribution in the three-dimensional image acquired on the day of treatment and a dose distribution in treatment plan data designed in advance; and a selection part that is configured to select whether or not to change the treatment plan data based on the dose distribution in the three-dimensional image acquired on the day of treatment and the dose distribution in treatment plan data designed in advance, wherein the treatment plan data is configured to be updated with the treatment plan data that has been changed based on the selection made by the selection part.

There is also presented an embodiment a particle beam treatment management method comprising: a three-dimensional image acquisition step of acquiring a three-dimensional internal image on a day of treatment in a treatment room; a dose distribution display step of displaying a dose distribution in the three-dimensional image acquired on the day of treatment and a dose distribution in the treatment plan data designed in advance; a selection step of selecting whether or not to change the treatment plan data based on the dose distribution in the three-dimensional image acquired on the day of treatment and the dose distribution in treatment plan data designed in advance; and an update step of updating the treatment plan data with the treatment plan data that has been changed based on selection made in the selection step.

According to an embodiment, even when the fixed position of an affected part or conditions of internal organs differ from the treatment plan designed in advance, accurately irradiating an affected part with a particle beam can be realized.

Hereinafter, a particle beam treatment system and a particle beam treatment management system according to an embodiment of the present embodiment will be described with reference to the accompanied drawings.

Embodiment

Figure 1:
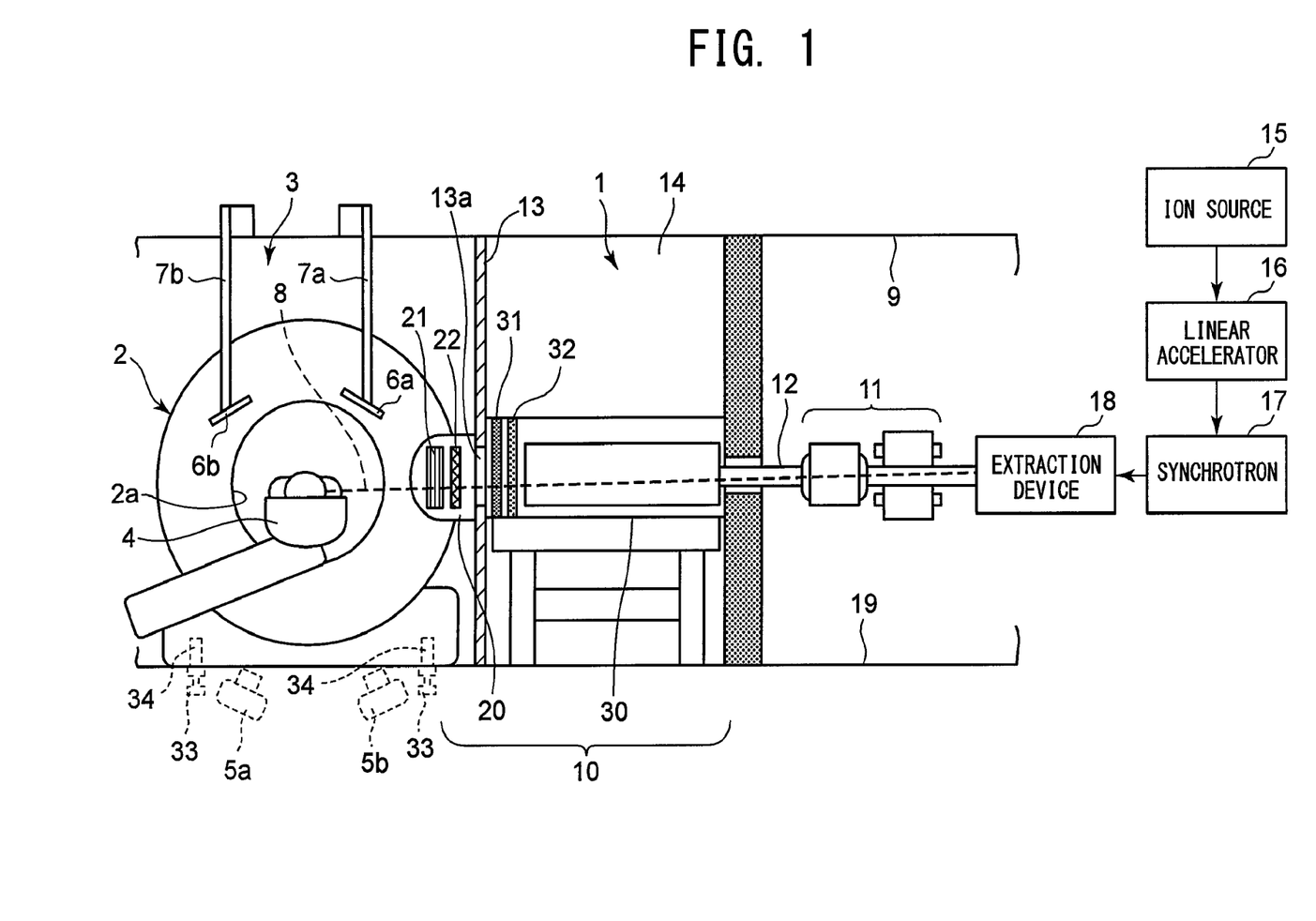
FIG. 1 is an elevational view illustrating the configuration of a scanning irradiation device to which a particle beam treatment system according to an embodiment is applied.

FIG. 1 is an elevational view illustrating the configuration of a scanning irradiation device to which a particle beam treatment system according to an embodiment is applied.

As illustrated in FIG. 1, the particle beam treatment system according to the present embodiment includes a scanning irradiation device 1 serving substantially as an irradiation part, a CT device 2, an X-ray photographing device 3, and a treatment bed 4. An irradiation port 10 of the scanning irradiation device 1, the CT device 2, the X-ray photographing device 3, and the treatment bed 4 are installed in a treatment room 14. The irradiation port 10 of the scanning irradiation device 1 is installed near the CT device 2 and within the moving range of the CT device 2 during its image acquisition (photographing process).

The X-ray photographing device 3 has two component sets. X-ray tubes 5a and 5b are installed inside a floor 19. The X-ray photographing device 3 includes flat panel detectors (hereinafter, abbreviated as "FPDs") 6a and 6b, and flat panel detector (FPD) drive mechanisms 7a and 7b. The FPDs 6a and 6b are attached to leading tips of the FPD drive mechanisms 7a and 7b, respectively. The FPD drive mechanisms 7a and 7b are installed on the ceiling 9. Thus, the X-ray photographing device 3 is configured to be able to acquire internal fluoroscopic images from two directions.

The FPDs 6a and 6b can be moved up and down by drive of the FPD drive mechanisms 7a and 7b. The FPDs 6a and 6b are located at lower positions when capturing the internal fluoroscopic images. When the CT device 2 is moved to the position of the treatment bed 4 at which CT photography is performed, the FPDs 6a and 6b are moved up to positions where they do not interfere with the CT device 2.

The scanning irradiation device 1 has, at its leading end, an irradiation port 10 that irradiates a patient placed on the treatment bed 4 with a beam. The irradiation port 10 includes an irradiation port movable part 20 and an irradiation port fixed part 30 which are separately formed from each other. The irradiation port movable part 20 can be moved horizontally with respect to the irradiation port fixed part 30 and is positioned within the moving range of the CT device 2. When the CT device 2 is moved to the position of the treatment bed 4, the irradiation port movable part 20 is horizontally moved to a position where it does not interfere with the CT device 2, that is, horizontally moved in a direction perpendicular to the paper surface of FIG. 1.

The scanning irradiation device 1 includes the irradiation port 10 disposed in the treatment room 14, scanning electromagnets 11 as beam scanning electromagnets installed outside the treatment room 14, and a vacuum duct 12. One end of the vacuum duct 12 is fixed to the upstream side of the irradiation port 10, and the other end thereof penetrates through the scanning electromagnets 11 and extends to an extraction device 18 of an accelerator to be described later.

The irradiation port movable part 20 is disposed downstream of a decorative wall 13 vertically installed in the treatment room 14 in the beam travel direction. In the irradiation port movable part 20, a range shifter 21 and a ridge filter 22 as range regulators are installed.

The irradiation port fixed part 30 is disposed upstream of the decorative wall 13 in the beam travel direction. In the irradiation port fixed part 30, a part of the vacuum duct 12, a position monitor 31, and a dose monitor 32 are installed.

The CT device 2 is of a self-moving type and configured to be movable to the treatment bed 4 along two rails 33 laid on the floor 19 in the treatment room 14 so as to extend in the perpendicular direction to the paper surface of FIG. 1. Specifically, the CT device 2 has a plurality of traveling wheels 34 running on the two rails 33, and one of the traveling wheels 34 is connected to an unillustrated driving motor. When the driving motor is driven, the traveling wheels 34 run along the two rails 33, whereby the CT device 2 can be moved to the treatment bed 4.

During CT photography performed by the CT device 2, the irradiation port movable part 20 is located at a position where it can interfere with the CT device 2. In such a case, the irradiation port movable part 20 is moved horizontally to prevent interference with the CT device 2.

The treatment bed 4 is configured to be movable up and down, and left and right by a positioning device to be described later for fine adjustment of the position of the affected part of the patient placed thereon.

Next, functions of respective devices provided in the scanning irradiation device 1 will be described.

An ion source 15, a linear accelerator 16, and a synchrotron 17 constitute a beam generation part of the present embodiment. Specifically, in the beam generation part, a beam is generated in such a manner that the linear accelerator 16 and the synchrotron 17 accelerate ions generated by the ion source 15 up to the energy level that can penetrate deep into the affected part.

That is, the linear accelerator 16 accelerates the ions generated by the ion source 15. The synchrotron 17 receives the beam accelerated by the linear accelerator 16 and circulates the beam to thereby further accelerate the beam to a predetermined energy level. After the beam acceleration, the beam is extracted by the extraction device 18 and transported to the vacuum duct 12 penetrating through the scanning electromagnets 11.

The scanning electromagnets 11 scan the particle beam 8 incident thereon at a point (X, Y) on a plane (slice plane) perpendicular to the beam axis in the affected part in the body. The beam scanning is performed by controlling an output current from a not illustrated power supply for scanning electromagnet.

The range shifter 21 controls the beam axis direction position (Z) in the affected part in the body. The range shifter 21 is constituted of a plurality of acrylic plates having different thicknesses and can change stepwise the energy level of the beam passing through the range shifter 21, i.e., internal range of the beam in accordance with the slice plane of the affected part by combining the acrylic plates. Generally, the internal range is changed stepwise by the range shifter 21 at a constant interval. Alternatively, the internal range change method may be a method that changes the energy level of beam itself by electrically controlling a device installed at the beam upstream side, or a method that inserts an object into a beam line as the range shifter 21 does.

The ridge filter 22 increases a very sharp peak dose (called Bragg peak) of a single-energy particle beam in the intracorporeal depth direction in accordance with the interval of the internal range changed by the range shifter 21.

The ridge filter 22 for scanning irradiation is constituted by arranging a plurality of aluminum bars. The bars are each formed into a substantially isosceles triangular shape in cross-section, and the energy level of beam is changed by differences in beam path length.

The position monitor 31 determines whether or not the position of the beam scanned by the scanning electromagnets 11 is located at an appropriate position. The position monitor 31 has the same configuration as that of the dose monitor 32. As the position monitor 31, e.g., one of a type divided into short strips (strip type) or one of a type having a collecting electrode constituted of a plurality wires in a vessel (multi-wire type) is available.

The dose monitor 32 measures irradiation dose and uses an ionization chamber or the like that collects, using parallel electrodes, a charge generated in a vessel by ionization effect of the particle beam.

Figure 2:
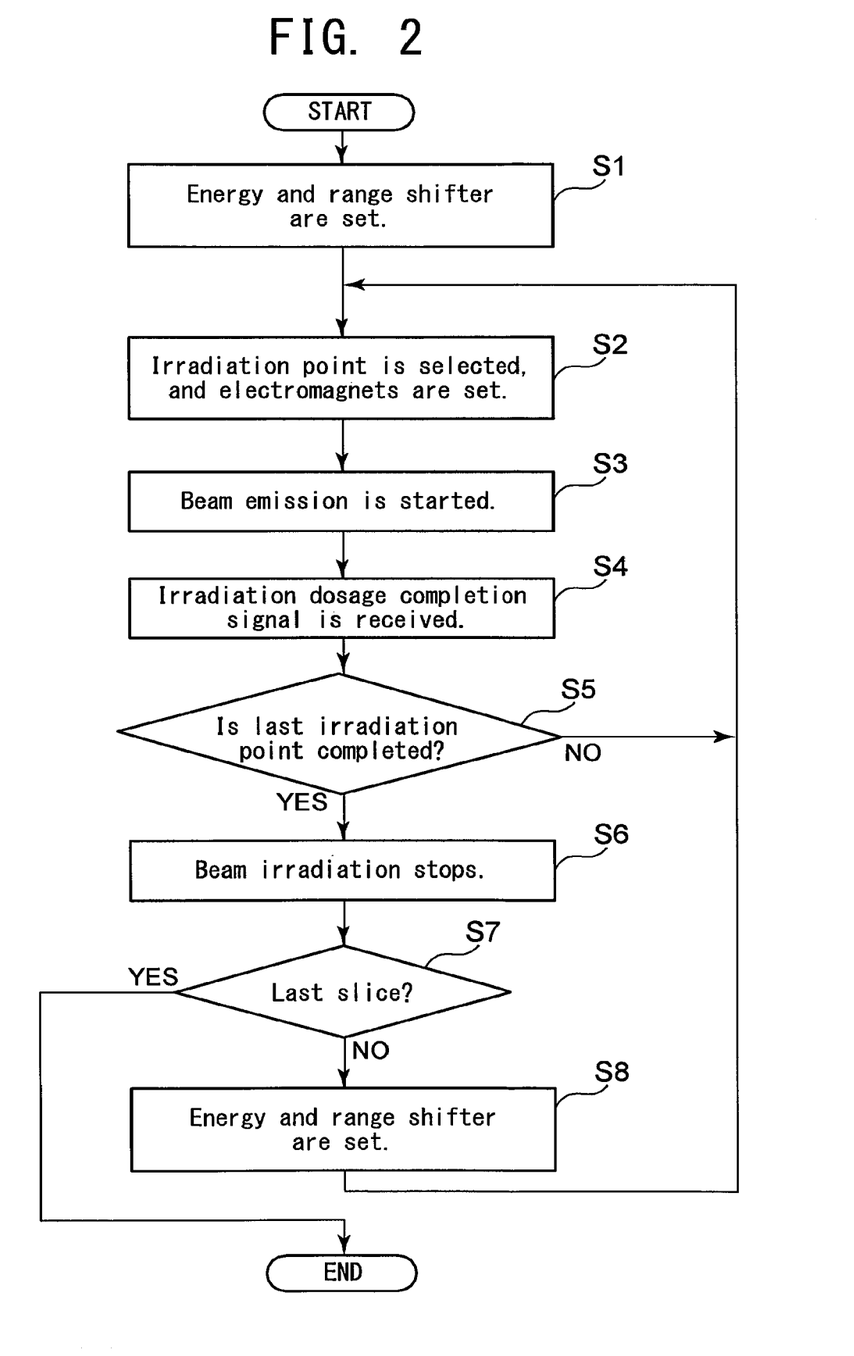
FIG. 2 is a flowchart illustrating an example of an irradiation procedure using the scanning irradiation device shown in FIG. 1.

Using the thus configured scanning irradiation device 1, scanning irradiation is performed by the following procedure. FIG. 2 is a flowchart illustrating an example of an irradiation procedure using the scanning irradiation device shown in FIG. 1.

As illustrated in FIG. 2, an incident energy of the particle beam and a plate thickness of the range shifter 21 are set such that the stop position of the particle beam corresponds to the deepest slice (Z1) of an affected part irradiation area (step S1).

Then, current values of the scanning electromagnets 11 are set such that the beam is irradiated onto a point (X1, Y1, Z1) in the affected part irradiation area in the target slice (step S2). After setting the beam position (X1, Y1, Z1), an unillustrated irradiation controller outputs an instruction signal to a beam emission controller. Then, the beam is emitted to irradiate the set point (step S3).

The irradiation controller holds a radiation dose (preset value) calculated to each point in advance. When a dose measurement value at the first point (X1, Y1, Z1) output from the dose monitor 32 reaches the preset value, the irradiation controller receives a dose termination signal and then outputs a current switching instruction signal to the power supply for the scanning electromagnets 11. Accordingly, the beam position is changed to the next point (X2, Y2, Z1) (step S4).

Meanwhile, there are known irradiation methods called a spot scanning method and a raster scanning method. The spot scanning method is a method in which emission of the particle beam is temporarily stopped between the time when the irradiation controller outputs the current switching instruction signal and the time when it receives a switching completion instruction signal from the power supply for the scanning electromagnets 11. The raster scanning method is a method in which emission of the particle beam is not stopped even during the current switching of the power supply for the scanning electromagnets 11.

Thereafter, every time the dose measurement value reaches the preset value, the current switching of the power supply for the scanning electromagnets 11 is performed. Then, when the irradiation to the last irradiation point (XN, YN, Z1) in the target slice is completed, the beam emission is stopped, and the plate thickness of the range shifter 21 is changed, whereby the target slice is changed to a slice one step before the deepest slice (steps S5 and S6).

At this time, the current values of the scanning electromagnets 11 are set such that the beam is irradiated onto a point (X1, Y1, Z2) in the affected part irradiation area in the current target slice. Then, the irradiation is performed onto the irradiation area in the current target slice in the same manner as irradiation onto the irradiation area in the previous slice.

The above irradiation process is sequentially performed until the last slice, and when the irradiation of all the slices is completed, a series of the irradiation processes is ended (step S7).

When the irradiation onto the last slice is yet to be performed in step S7, another incident energy of the particle beam and another plate thickness of the range shifter 21 are set (step S8). Thereafter, steps S2 to S7 are performed for the last slice, and when the irradiation of all the slices is completed, a series of the irradiation processes is ended.

Next, the entire configuration of a particle beam treatment system according to the present embodiment will be described.

Figure 3:
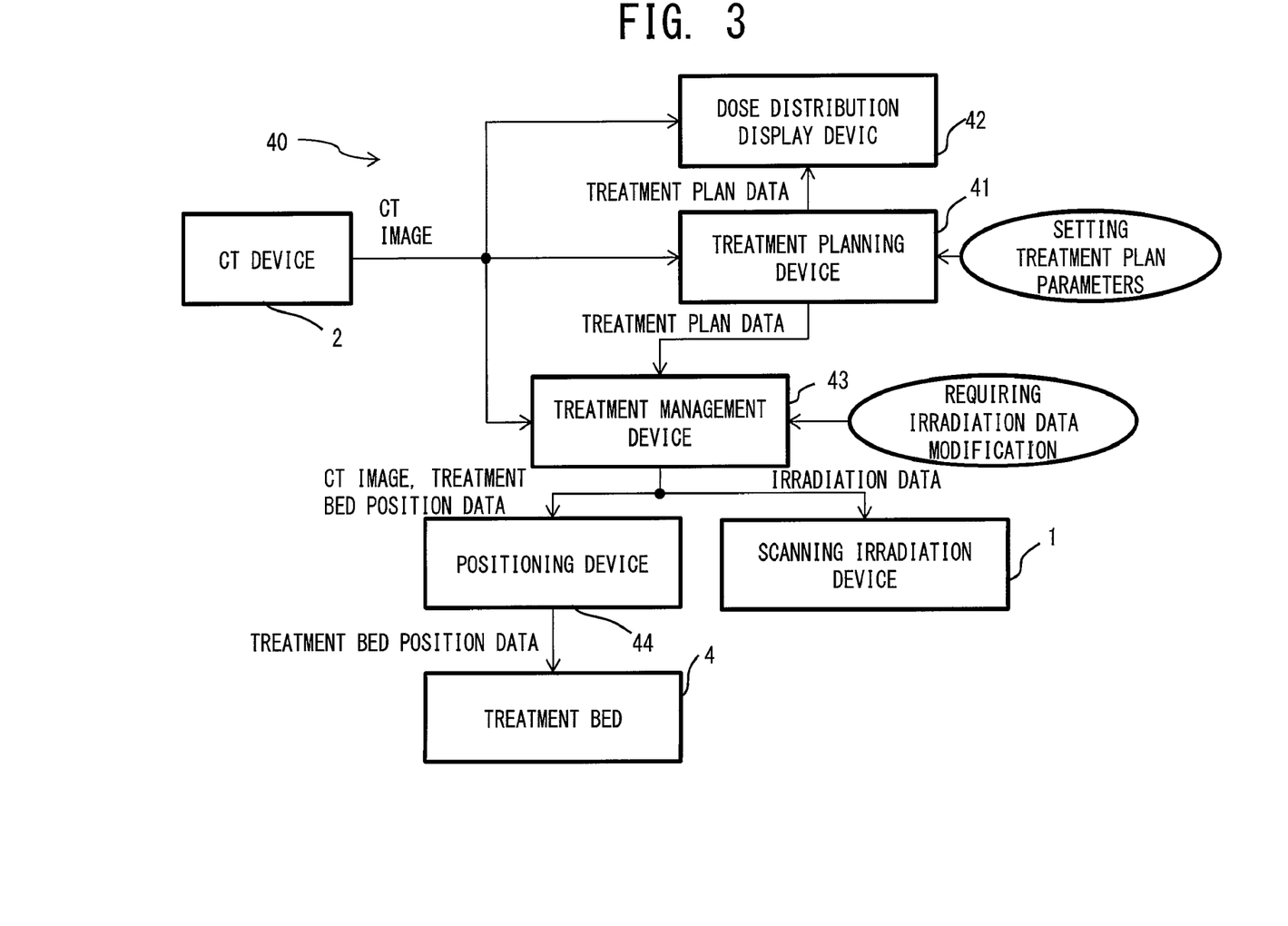
FIG. 3 is a block diagram illustrating a control system of the particle beam treatment system according to the present embodiment.

FIG. 3 is a block diagram illustrating a control system of the particle beam treatment system according to the present embodiment.

As illustrated in FIG. 3, a particle beam treatment system 40 includes a treatment planning device 41 as a calculation part, a dose distribution display device 42, a treatment management device 43, a positioning device 44, the treatment bed 4, the scanning irradiation device 1 as an irradiation part, and the CT device 2 as a three-dimensional image acquisition part. The CT device 2 acquires a three-dimensional image of the affected part of a patient immediately before treatment (on the day of the treatment) in the treatment room 14.

The treatment management device 43 has functions as a selection part, a deviation amount evaluation part, and an irradiation position correction part according to the present embodiment. The treatment planning device 41, the dose distribution display device 42, and the treatment management device 43 constitute a particle beam treatment management system according to the present embodiment.

The particle beam treatment system 40 of the present embodiment uses the CT device 2 as the three-dimensional image acquisition part; however, instead of the CT device 2, it may also use image diagnosis devices capable of acquiring a three-dimensional image, such as an MRI (Magnetic Resonance Imaging) device, a PET (Positron Emission Tomography)-CT device.

The treatment planning device 41 sets target isocenter (affected part center) information, beam angle information, region of interest (ROI; affected part area) information, and position information of normal organ whose exposure to irradiation should be avoided, based on a three-dimensional internal image acquired from the CT device 2. The treatment planning device 41 further performs optimization calculation of irradiation dose to the affected part to thereby create setting information to be set to the treatment bed 4 and irradiation data (pattern) to be described later.

Hereinafter, the target isocenter information (affected part center) information, the beam angle information, the region of interest (ROI) information, and the position information of normal organ whose exposure to irradiation should be avoided, the irradiation position information, the position setting data of the treatment bed 4, and the irradiation data (pattern) to be described later are collectively referred to also as "treatment plan data".

The irradiation data described above is data indicating how to perform irradiation onto the irradiation area. Specifically, the irradiation data is data in which the irradiation dose to each irradiation spot is weighted so as to make a dose distribution in the affected part uniform.

The treatment planning device 41 can reuse at least one of setting parameters in the treatment plan designed in advance, for the three-dimensional internal image newly set by the CT device 2. The setting parameters in the treatment plan include, e.g., the target isocenter (affected part center) information, the beam angle information, the region of interest information, and the position information of normal organ whose exposure to irradiation should be avoided. Further, the treatment planning device 41 can reuse a slice interval and a spot interval as a device setting parameter required to create the irradiation data. Among the above information items, any items not to be reused can be reset to new ones.

The region of interest (ROI) information and the position information of normal organ whose exposure to irradiation should be avoided are cross-sectional image information of a three-dimensional image. When the treatment planning device 41 of the present embodiment sets a positional deviation amount or an irradiation area to one cross section image, the positional deviation amount or the irradiation area can automatically be set to other cross-section images as well.

The dose distribution display device 42 displays the newly acquired three-dimensional image and the region of interest information set in advance, the position information of normal organ whose exposure to irradiation should be avoided, and an irradiation dose distribution. That is, the dose distribution display device 42 applies the treatment plan data designed in advance, to the three-dimensional image acquired immediately before treatment, to calculate a dose distribution. Thus, the dose distribution display device 42 displays an irradiation dose distribution in the affected part and the normal organ. Those functions are often provided in the treatment planning device 41.

While the treatment planning device 41 and the dose distribution display device 42 each may be used by being connected to the particle beam treatment system as a device independent of the particle beam treatment system, they are included in the particle beam treatment system in the present embodiment.

The treatment management device 43 has a function of selecting whether or not to perform the positioning of the patient using the positioning device 44, and whether or not to change the treatment plan data designed in advance, so as to correct the position of the treatment bed 4 on which the patient is placed.

The treatment management device 43 has a function of evaluating the deviation amount of the irradiation position based on the three-dimensional internal image acquired immediately before treatment (on the day of the treatment), an irradiation position correction function of performing correction for irradiation position data of the treatment plan data designed in advance, a calculation function of performing optimization calculation of the irradiation data in the treatment plan data, and a selection function of selecting one of the above functions.

The treatment management device 43 also has a function of setting irradiation position information having a corrected irradiation position to the scanning irradiation device 1, in addition to the irradiation data in the treatment plan data designed in advance. Further, the treatment management device 43 also has a function of setting newly optimized irradiation data to the scanning irradiation device 1 without changing the position information of the treatment bed 4.

Next, a procedure of treatment performed using the particle beam treatment system according to the present embodiment will be described.

Figure 4:
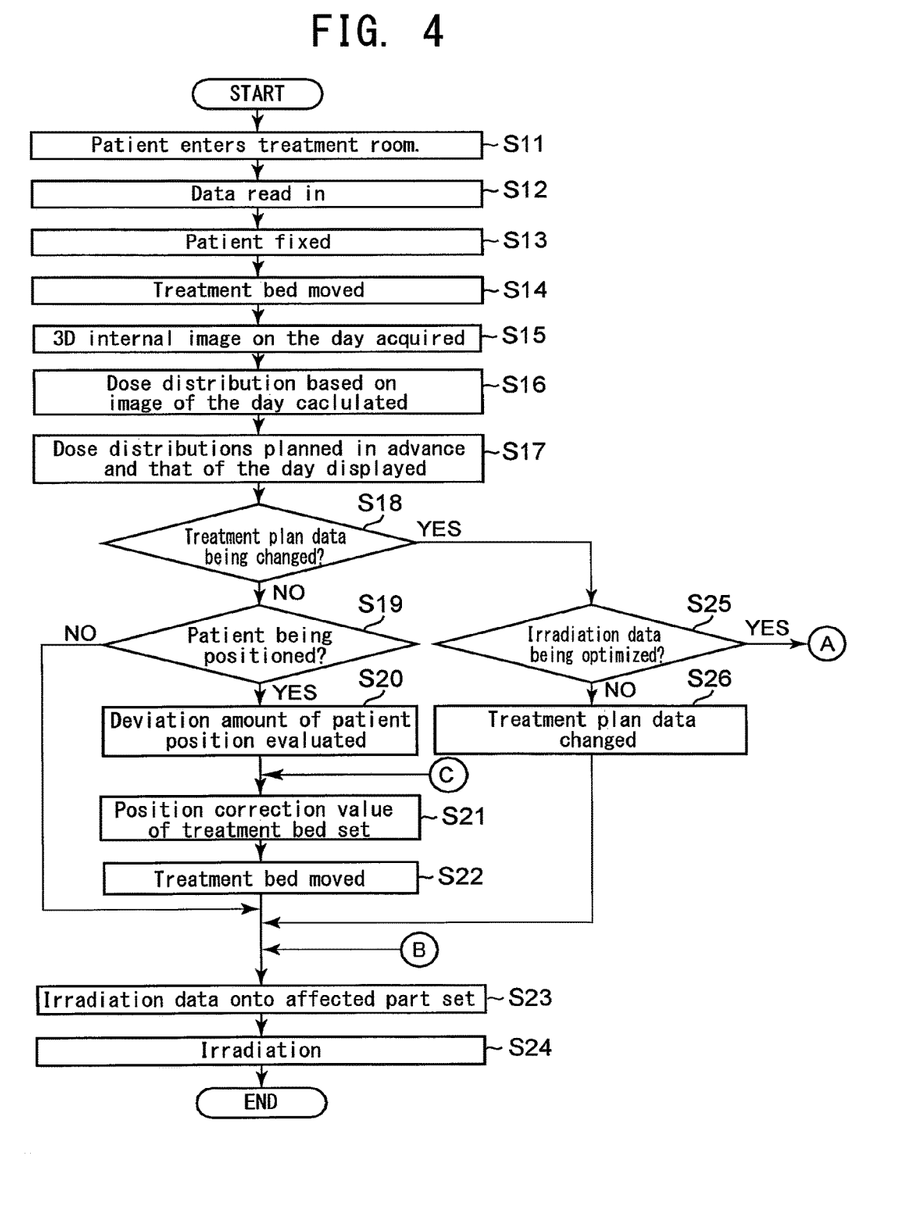
FIG. 4 is a flowchart illustrating an example of the procedure of treatment performed using the particle beam treatment system according to the embodiment.
Figure 5:
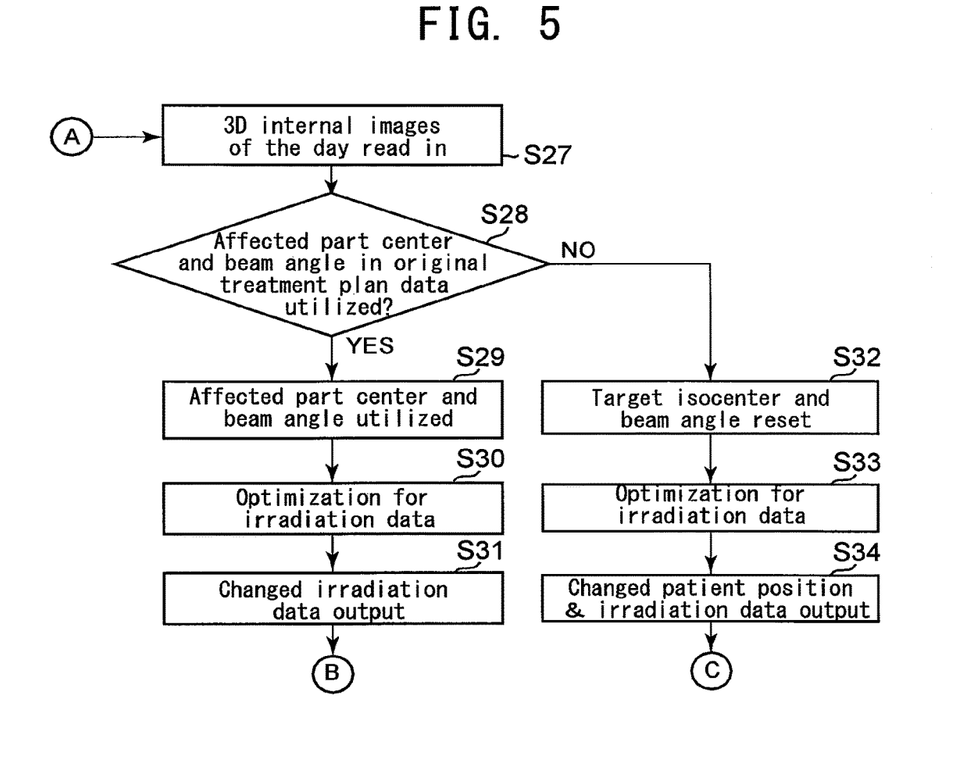
FIG. 5 is a flowchart illustrating processing performed by the treatment planning device according to the embodiment.
Figure 6:
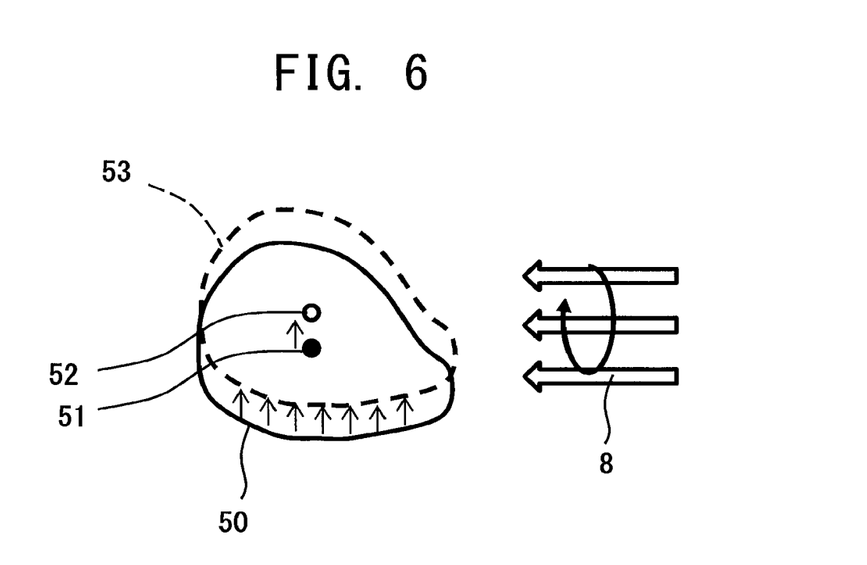
FIG. 6 is an explanatory view illustrating an irradiation area obtained when the particle beam treatment system of the embodiment performs a correction of the position of treatment bed.
Figure 7:
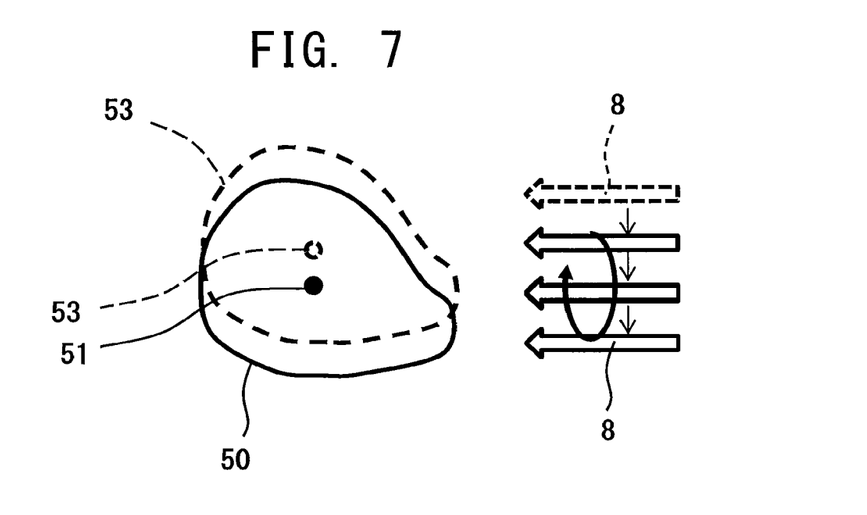
FIG. 7 is an explanatory view illustrating an irradiation area obtained when the particle beam treatment system of the embodiment changes the treatment plan data.
Figure 8:
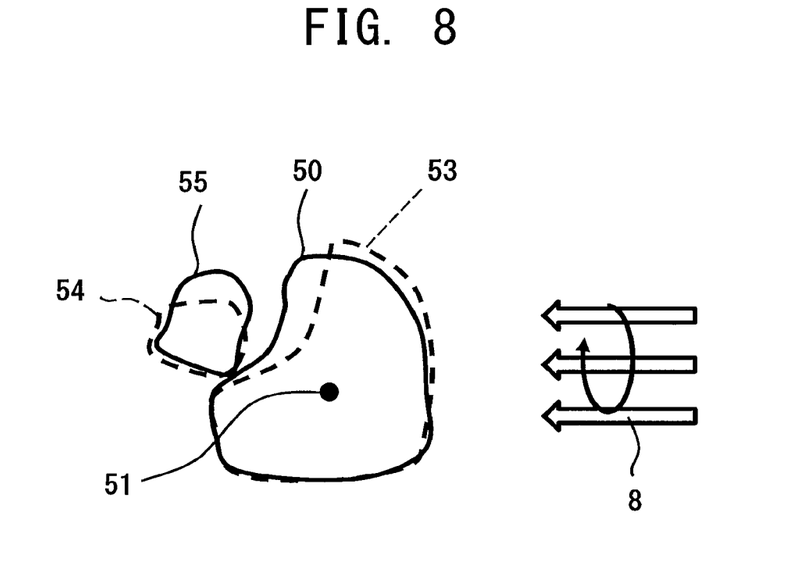
FIG. 8 is an explanatory view illustrating region of interest information and position information of normal organ whose exposure to irradiation should be avoided when the treatment planning device of the embodiment uses the target isocenter and the beam angle information.

FIG. 4 is a flowchart illustrating an example of the procedure of treatment performed using the particle beam treatment system according to the embodiment. FIG. 5 is a flowchart illustrating processing performed by the treatment planning device according to the embodiment. FIG. 6 is an explanatory view illustrating an irradiation area obtained when the particle beam treatment system of the embodiment performs a correction of the position of treatment bed. FIG. 7 is an explanatory view illustrating an irradiation area obtained when the particle beam treatment system of the embodiment changes the treatment plan data. FIG. 8 is an explanatory view illustrating region of interest information and position information of normal organ whose exposure to irradiation should be avoided when the treatment planning device of the embodiment uses the target isocenter and the beam angle information.

First, CT photography is performed in the treatment room 14 where the CT device 2 has been installed to acquire three-dimensional images in advance (before the treatment day). At this time, an estimated center position of the affected part is marked on the surface of the fixing tool for fixing the patient to the treatment bed 4.

Then, CT images acquired in the treatment room 14 are used to design a treatment plan. In this treatment plan, an irradiation area is set, and irradiation data (irradiation pattern) indicating how to perform irradiation onto the irradiation area and position setting data of the treatment bed 4 are created.

Next, the procedure of treatment performed by the particle beam treatment system of the present embodiment immediately before treatment (on the data of the treatment) will be described with reference to FIGS. 4 and 5.

The treatment plan data designed in advance, i.e., the position setting data of the treatment bed 4 and the irradiation data concerning the treatment are read from the treatment planning device 41 into the treatment management device 43 immediately before or at the time when the patient enters the treatment room 14 (steps S11 and S12).

Then, the patient who has entered the treatment room 14 is placed on the treatment bed 4 and fixed thereto by the fixing tool (step S13). Then, in the treatment room 14, the positioning device 44 is used to move the treatment bed 4 so as to make the mark put on the fixing tool meet with the target isocenter (affected part center). Further, the treatment management device 43 sets the position setting data to the treatment bed 4, and then an input device of the treatment bed 4 is operated to move the treatment bed 4 to the position indicated by the position setting data (step S14).

Then, the treatment planning device 41 retreats the irradiation port movable part 20 from the irradiation position, sets a measurement part (gantry) 2a of the CT device 2 to the region of interest, and performs CT photography (step S15). That is, in step S15, the treatment planning device 41 uses the CT device 2 to acquire three-dimensional internal images on the day of the treatment. The treatment planning device 41 calculates a dose distribution based on the acquired three-dimensional images (step S16) and transmits the dose distribution data to the dose distribution display device 42.

The dose distribution display device 42 displays a dose distribution based on the treatment plan designed in advance and a dose distribution based on the three-dimensional internal images on the day of the treatment side by side or in an overlaying manner (step S17).

Subsequently, it is selected whether or not to change the treatment plan data designed in advance (step S18), and it is selected whether or not to correct the position of the treatment bed 4 on which the patient is placed (step S19). That is, in step S19, it is selected whether or not to perform positioning for correcting the position of the patient. The selections in steps S18 and S19 are performed by operating an input/output device of the treatment management device 43. In the present embodiment, it is assumed that the selections in steps S18 and S19 are made by a medical staff; however, alternatively, the selections may be made automatically based on evaluation of a difference between the comparison results displayed in step S17.

When it is selected that the treatment plan data is not changed (NO in step S18) and that the position of the treatment bed 4 is corrected (YES in step S19), the treatment management device 43 compares CT images acquired this time and the CT images (reference images) acquired in the treatment room 14 in advance to evaluate the deviation amount of the position of the affected part (step S20).

Then, the treatment management device 43 sets a position correction value of the treatment bed 4 based on the deviation amount of the position of the affected part (step S21). Further, the treatment management device 43 transmits position correction values to the treatment bed 4 to move the treatment bed 4 by the amount corresponding to the position correction values for positioning of the patient (step S22) (3D-3D positioning).

That is, as illustrated in FIG. 6, the target isocenter (affected part center) 51 in the treatment plan is set in the irradiation area 50 for which the treatment plan is designed in advance. In the present embodiment, the treatment bed 4 is moved based on the deviation amount of the position of the affected part so as to make the affected part center and a treatment device isocenter 52 meet with each other. At this time, calculation results of the irradiation data obtained before the treatment day is used as the irradiation data. That is, the irradiation pattern of the particle beam 8 is not influenced.

Then, after completion of the positioning of the patient, the measurement part (gantry) 2a of the CT device 2 is retreated, and the irradiation port movable part 20 is returned to a predetermined position. After that, affected part irradiation data is set to the scanning irradiation device 1, and an irradiation start button of an unillustrated irradiation console is depressed to start irradiation onto the affected part (steps S23 and S24).

When it is selected that the position of the treatment bed 4 on which the patient is placed is not corrected (NO in step S19), steps S20 to S22 are skipped to directly set the affected part irradiation data in step S23.

When it is selected that the treatment plan data is changed (YES in Step S18), the treatment management device 43 determines whether or not to perform optimization calculation for the irradiation data in the treatment plan data (step S25). When it is determined that optimization calculation by the treatment planning device 41 is not performed (NO in step S25), the treatment plan data is changed (step S26). In step S26, only the spot position (X, Y) and slice setting (Z) in the irradiation data are changed, and the weighting applied to the irradiation dose to each irradiation spot is not changed.

In the present embodiment, when the treatment device isocenter 52 and the target isocenter (affected part center) 51 in the treatment plan are deviated from each other as illustrated in FIG. 7, the treatment bed 4 is not moved, but the irradiation position of the particle beam 8 is moved by the deviation amount to thereby adjust the irradiation area to the affected part.

Specifically, when the treatment plan data is changed in the treatment management device 43, the CT images acquired this time and CT images (reference images) acquired in the treatment room 14 in advance are compared to evaluate the deviation amount of the position of the affected part, and then the irradiation position information of the treatment plan data is moved in parallel by the deviation amount of the affected part position.

In the present embodiment, the irradiation position is moved in parallel to change the treatment plan data as described above. Alternatively, for example, the irradiation energy level may be varied to change the range. In the case of a scanning irradiation device having a rotary gantry, the beam angle information may also be changed for correction.

After completion of the change processing of the treatment plan data in step S26, the measurement part 2a of the CT device 2 is retreated, and the irradiation port movable part 20 is returned to a predetermined position in the same manner as described above. Then, the treatment plan data in which the irradiation position has been changed is applied to the scanning irradiation device 1 to set the affected part irradiation data thereto, and the irradiation start button of the unillustrated irradiation console is depressed to start irradiation onto the affected part (steps S23 and S24).

When it is selected in the treatment management device 43 that optimization calculation for the irradiation data is performed (YES in step S25), the optimization calculation is performed by the treatment planning device 41. Specifically, as illustrated in FIG. 5, the treatment planning device 41 reads in the CT images acquired on the day of the treatment in step S15 (step S27).

Then, the treatment management device 43 determines whether or not to utilize the affected part center information and the beam angle information in the original treatment plan data (step S28). When it is determined that the affected part center information and the beam angle information in the original treatment plan data are utilized (YES in step S28), these information items are utilized (step S29).

In this case, as illustrated in FIG. 8, the target isocenter (affected part center) 51 which was acquired in the treatment plan, using the CT images obtained in the treatment room 14, the beam angle, the region of interest (ROI) information indicating the irradiation area 50 of the affected part designed in advance, and position information of the normal organ 54 whose exposure to irradiation should be avoided are read. Further, as device setting parameters required to create the irradiation data, the slice interval and the spot interval are read in. Then, the target isocenter 51 and the beam angle are set as setting conditions for the optimization calculation. The region of interest information indicating the irradiation area 50 of the affected part and the position information of the normal organ 54 are overlaid on an irradiation area 53 and the normal organ 44 in the CT images acquired on the day of the treatment. When the irradiation areas 50 and 53 of the affected part and/or the normal organs 54 and 55 are deviated from each other, respectively, the areas are corrected.

Corrections of the region of interest and the normal organ area are made for one cross section of the CT image first. A variation in the centroid of each of these areas and a deformation thereof due to the correction are automatically reflected on the other cross sections, whereby all cross-sections of the CT image are corrected.

Then, the treatment planning device 41 performs the optimization calculation for the irradiation data again (step S30). In the optimization calculation for the irradiation data, the region of interest (ROI) information indicating the irradiation area 50 of the affected part is set to all slices of the affected part, and the affected part center information and beam angle information are set to a representative slice of the affected part, and other parameters are set together with the position information of normal organ 54 whose exposure to irradiation should be avoided. Then, the position and the weight of each spot in the irradiation data are reset.

After performing the irradiation data optimization calculation again, the treatment planning device 41 checks the result of the dose distribution. When there is no problem, the treatment planning device 41 rewrites the treatment plan data and transmits it to the treatment management device 43. At this time, the target isocenter 51 and the beam angle are not changed as described above, so that the position information of the treatment bed 4 is not changed.

After receiving the new treatment plan data, the treatment management device 43 retreats the measurement part 2a of the CT device 2 and returns the irradiation port movable part 20 to a predetermined position. At this time, the setting value of the treatment bed 4 is not changed, so that the treatment bed 4 need not be moved. Then, after outputting the optimization-calculated irradiation data to the scanning irradiation device 1 (step S31), the treatment management device 43 rewrites the affected part irradiation data based on the optimization-calculated irradiation data. Then, the irradiation start button of the unillustrated irradiation console is depressed to start irradiation onto the affected part (steps S23 and S24).

When there is any problem with the dose distribution after the optimization calculation is performed again using values of the target isocenter 51 and the beam angle in the previous treatment plan data, or when it is obvious that these values need to be reset (NO in step S28), the treatment planning device 41 rests the target isocenter 51 and the beam angle (step S32) to redesign the treatment plan. After that, the treatment planning device 41 transmits the redesigned treatment plan data to the treatment management device 43.

After receiving the new treatment plan data, the treatment management device 43 retreats the measurement part 2a of the CT device 2 and returns the irradiation port movable part 20 to the predetermined position. At this time, the setting value of the treatment bed 4 is changed, so that the treatment bed 4 is moved. Then, the irradiation data optimization calculation is performed again (step S33) in a similar way as in step S30.

After that, the treatment management device 43 outputs the position setting data to the treatment bed 4, and outputs the optimization-calculated irradiation data (step S34). Then, the processing flow shifts to step S21.

Thus, in the particle beam treatment system of the present embodiment, the treatment plan data designed in advance is applied to the three-dimensional image acquired immediately before the treatment to calculate a dose distribution, and then an irradiation dose to the affected part or normal organ is displayed.

According to the thus configured present embodiment, the treatment plan data designed in advance can be changed immediately before treatment, so that even when the fixed position of the affected part or the condition of the internal organ differs from that in the treatment plan designed in advance, the particle beam can be irradiated correctly onto the affected part.

Further, according to the present embodiment, the irradiation area of the affected part can be set based on the three-dimensional internal image obtained immediately before the treatment, so that even when the position of the affected part and the position of the normal organ have been changed from those at the acquisition time of the three-dimensional image used for the treatment plan designed in advance, the beam can be irradiated onto the affected part with high accuracy while avoiding irradiation onto the normal tissue.

This eliminates the need to move the treatment bed 4, thus eliminating the need to consider positional reproducibility of the treatment bed 4, which can simplify QA with respect to daily adjustment of the treatment bed position. Further, since there is no need to move the treatment bed 4, the time for resetting the treatment bed 4 becomes unnecessary. Further, there is no need to perform X-ray photography for confirming whether the position of the treatment bed 4 after movement is correct, device setting time for X-ray photography becomes unnecessary. As a result, the time required for treatment can be reduced to thereby reduce radiation dose to the patient.

Further, according to the present embodiment, a function as the irradiation position correction part that performs correction of the irradiation position in the treatment plan data designed in advance is provided, thereby eliminating the need to perform the optimization calculation for the treatment plan, which can reduce the time from acquisition of the three-dimensional internal image to the start of irradiation.

Further, according to the present embodiment, the target isocenter 51 and the beam angle information in the treatment plan designed in advance can be utilized. Thus, when a result of the dose optimization calculation is set to the scanning irradiation device 1, the position of the treatment bed 4 need not be reset. This eliminates the time required to reset the treatment bed 4. Further, since there is no need to perform X-ray photography for confirming whether the position of the treatment bed 4 after movement is correct, device setting time for X-ray photography becomes unnecessary. As a result, the time required for treatment can be reduced.

Further, according to the treatment planning device 41 of the present embodiment, since the region of interest information or the position information of the normal organ whose exposure to irradiation should be avoided in the treatment plan designed in advance can be utilized, the time required to design the treatment plan can be reduced. Further, when a positional deviation amount of the region of interest information or the position information of the normal organ whose exposure to irradiation should be avoided is set to one cross section of the cross-sectional image of the three-dimensional image, the deviation amount can be automatically set to other cross-sections, thereby reducing the work load on the doctor or the radiation technologist.

OTHER EMBODIMENTS

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Generally, in the above embodiment, the particle beam treatment is performed for several days with irradiation dose divided into a plurality of individual doses. Further, although, in the above description of the embodiment, the setting parameters of the treatment plan for the CT image acquired in the treatment room 14 are used as a base point, setting parameters obtained by performing recalculation in the treatment room 14 may be used as a base point from the second time.

In the above description, the reference symbols are as follows:

1: scanning irradiation device (irradiation part); 2: CT device (three-dimensional image acquisition part); 2a: measurement part; 3: X-ray photographing device; 4: treatment bed; 5a, 5b: X-ray tube; 6a, 6b: flat panel detector (hereinafter (FPD); 7a, 7b: FPD drive mechanism; 8: particle beam; 9: ceiling; 10: irradiation port; 11: scanning electromagnet; 12: vacuum duct; 13: decorative wall; 14: treatment room; 15: ion source; 16: linear accelerator; 17: synchrotron; 18: extraction device; 19: floor; 20: irradiation port movable part; 21: range shifter; 22: ridge filter; 30: irradiation port fixed part; 31: position monitor; 32: dose monitor; 33: rail; 34: traveling wheel; 40: particle beam treatment system; 41: treatment planning device; 42: dose distribution display device (dose distribution display part); 43: treatment management device (selection part; deviation amount evaluation part; calculation part; irradiation position correction part); 44: positioning device; 50: irradiation area; 51: target isocenter; 52: treatment device isocenter; 53: irradiation area; 54: normal organ; and 55: normal organ.

What is claimed is:

1. A particle beam treatment system comprising:
 a three-dimensional image acquisition part installed in a treatment room for acquisition of a three-dimensional internal image on a day of treatment;
 a dose distribution display part that is configured to display a dose distribution in the three-dimensional image acquired on the day of treatment and a dose distribution in treatment plan data designed in advance;
 a selection part that is configured to select whether or not to change the treatment plan data based on the dose distribution in the three-dimensional image acquired on the day of treatment and the dose distribution in treatment plan data designed in advance; and
 an irradiation part that is configured to irradiate an affected part with a particle beam according to the treatment plan data based on selection made by the selection part.

2. The particle beam treatment system according to claim 1, further comprising a treatment planning device that is configured to perform dose optimization calculation of irradiation data indicating the position and weight of each irradiation spot of the affected part in the treatment plan data when the treatment plan data is changed based on the selection made by the selection part.

3. The particle beam treatment system according to claim 1, further comprising:
 a deviation amount evaluation part that is configured to evaluate the deviation amount of the irradiation position of the affected part in the treatment plan data designed in advance based on the three-dimensional image acquired on the day of treatment; and
 an irradiation position correction part that is configured to correct the irradiation position in the treatment plan data based on the deviation amount evaluated by the deviation amount evaluation part.

4. The particle beam treatment system according to claim 1, wherein
 the treatment plan data includes affected part center information, beam angle information, region of interest information, and position information of normal organ whose exposure to irradiation should be avoided.

5. The particle beam treatment system according to claim 4, wherein
 the treatment planning device reuses at least one of the affected part center information, the beam angle information, the region of interest information, the position information of normal organ whose exposure to irradiation should be avoided, a slice interval, and a spot interval for the three-dimensional image obtained on the day of treatment.

6. The particle beam treatment system according to claim 4, wherein
 the treatment planning device is configured to be able to reset at least one of the affected part center information, the beam angle information, the region of interest information, the position information of normal organ whose exposure to irradiation should be avoided, a slice interval, and a spot interval for the three-dimensional image obtained on the day of treatment.

7. The particle beam treatment system according to claim 5, wherein
 the treatment planning device is configured to perform dose optimization calculation using the information to be reused.

8. The particle beam treatment system according to claim 6, wherein
the treatment planning device is configured to perform dose optimization calculation using the information to be reset.

9. A particle beam treatment management system comprising:
a three-dimensional image acquisition part installed in a treatment room for acquisition of a three-dimensional internal image on the day of treatment;
a dose distribution display part that is configured to display a close distribution in the three-dimensional image acquired on the day of treatment and a dose distribution in treatment plan data designed in advance; and
a selection part that is configured to select whether or not to change the treatment plan data based on the dose distribution in the three-dimensional image acquired on the day of treatment and the dose distribution in treatment plan data designed in advance, wherein
the treatment plan data is configured to be updated with the treatment plan data that has been changed based on the selection made by the selection part.

10. A particle beam treatment management method comprising:
a three-dimensional image acquisition step of acquiring a three-dimensional internal image on a clay of treatment in a treatment room;
a dose distribution display step of displaying a dose distribution in the three-dimensional image acquired on the day of treatment and a dose distribution in the treatment plan data designed in advance;
a selection step of selecting whether or not to change the treatment plan data based on the dose distribution in the three-dimensional image acquired on the day of treatment and the dose distribution in treatment plan data designed in advance; and
an update step of updating the treatment plan data with the treatment plan data that has been changed based on selection made in the selection step.

* * * * *